United States Patent [19]

Thomas

[11] Patent Number: 4,495,278
[45] Date of Patent: Jan. 22, 1985

[54] PROCESS FOR MAKING NOVEL BLOOD CLOTTING ENZYME COMPOSITIONS

[75] Inventor: William R. Thomas, Laguna Niguel, Calif.

[73] Assignee: Baxter Travenol Laboratories, Inc., Deerfield, Ill.

[21] Appl. No.: 258,072

[22] Filed: Apr. 27, 1981

[51] Int. Cl.³ .................. C12Q 1/70; C12Q 1/56; C12N 7/04; C12N 7/06; C12N 9/48; C12N 9/68; C12N 9/74

[52] U.S. Cl. .................. 435/5; 435/13; 435/212; 435/214; 435/217; 435/236; 435/238; 435/810; 435/814; 436/8; 436/16; 424/89; 424/94; 424/101

[58] Field of Search ............ 435/5, 13, 236, 238, 435/212, 214, 217, 188, 810, 814; 424/101, 12, 89, 93, 94; 252/408; 436/8, 16, 18

[56] References Cited

U.S. PATENT DOCUMENTS

| | | | |
|---|---|---|---|
| 3,041,242 | 6/1962 | Barr et al. | 424/101 |
| 3,100,737 | 8/1963 | Auerswald et al. | 424/101 |
| 3,539,450 | 11/1970 | Deutsch | 435/188 |
| 3,579,631 | 5/1971 | Stewart et al. | |
| 3,859,168 | 1/1975 | Barth et al. | 435/236 |
| 4,250,139 | 2/1981 | Luck et al. | 422/21 |
| 4,297,344 | 10/1981 | Schwinn et al. | 424/101 |
| 4,314,997 | 2/1982 | Shanbrom . | |
| 4,327,086 | 4/1982 | Fukushima et al. | 424/177 |

FOREIGN PATENT DOCUMENTS 2916711  11/1980  Fed. Rep. of Germany .
1471336   4/1977  United Kingdom .

OTHER PUBLICATIONS

Sigma Chemical Company Catalogue, St. Louis, Missouri, 143–145, (Feb. 1981).
Lawrence et al., Lea & Febiger, pp. 673–674 and 682–685, (1968).
Allen et al., J. Am. Med. Assoc., 144, (13): 1069–1074, (1950).
Kaplan, "J. Gen. Microbiol.", 18: 58–63, (1958).
Cowdery et al., "Develop. Biol. Standard.", 36: 297–303, (1977).
Beardmore et al., "Applied Microbiology", 16, (2): 362–365, (1968).
Deutsch et al. and Rozenberg et al., "XII International Congress on Blood Transfusion, Abstracts", pp. 472–475, (1969).
Tabor et al., "The Lancet", pp. 68–70, Jul. 12, 1980.
Scatchard et al., "J. Clin. Invest.", 24: 445–453, (1944).
Havens, "Proc. Soc. Exp. Biol. and Med.", 58: 203–204, (1945).
Bertrand et al., "Vox Sang.", 4: 385–402, (1959).
Roberts et al., "Thrombos. Diathes. Haemorrh.", 33: 610, (1975).
Kraft et al., "Proc. Soc. Exp. Biol. and Med.", 9: 306–309, (1954).
Soulier et al., "Amer. J. Dis. Child", 123: 429–434, (1972).
Paine et al., "J.A.M.A.", 150, (3): 199–202, (1952).
Schable et al., "Journal of Biological Standardization", 7: 293–299, (1979).
Berge et al., "Applied Microbiology", 22, (5): 850–853, (1971).
Greiff et al., "Journal of Immunology", 94, (3): 395–400, (1965).
Greiff et al., "Applied Microbiology", 16, (6): 835–840, (1968).
Plowright et al., "Res. Vet. Sci.", 11: 71–81, (1970).
Apostolov et al., "Cytobiology", 10:255–259, (1973).
Sirridge, *Laboratory Evaluation of Hemostasis*, pp. 7–8, (1974).
Chemical Abstracts, 76: 22760u, (1972).
Brozovic, "J. Clin. Path.", 24: 690–693, (1971).

*Primary Examiner*—Esther M. Kepplinger
*Attorney, Agent, or Firm*—Max D. Hensley; Marjorie D. Hunter; Paul C. Flattery

[57] ABSTRACT

Viruses, particularly hepatitis viruses, in blood clotting enzyme compositions are inactivated with little enzyme activity loss by heating the compositions in the dry state. The novel products which result are therapeutically and diagnostically useful.

87 Claims, 1 Drawing Figure

INACTIVATION KINETICS OF LYOPHILIZED SINDBIS VIRUS IN PROTHROMBIN COMPLEX CONCENTRATE AT SELECTED TEMPERATURES

PROCESS FOR MAKING NOVEL BLOOD CLOTTING ENZYME COMPOSITIONS

FIELD OF THE INVENTION

This invention relates to a method for the inactivation of viruses in compositions containing blood clotting factor enzymes, especially prothrombin and clotting factors VII, IX and X, to produce compositions which are no longer potentially hazardous to patients and medical personnel. In particular, this invention is concerned with inactivating viruses in prothrombin complex, a known therapeutic blood plasma fraction which is a mixture of prothrombin and factors VII, IX and X.

BACKGROUND OF THE INVENTION

The language "inactivation of virus", or "substantially free of infectious virus" as used herein means that the residual titer of biologically infectious virus in products treated according to the method described below is so low that infusion of therapeutic quantities of the product into a plurality of normal animal hosts for the virus in question will not produce statistically significant clinical or serological evidence of infection ($p<0.1$) in a statistically significant host population. This does not require that the products be sterilized, or completely free of virus, because compositions having a low viral titer may have therapeutic utility where the alternative is a more contaminated material.

Hageman factor, prothrombin and factors XI, VII, IX and X are all plasma proenzymes. They participate in a complex cascade of enzyme mediated reactions culminating in the conversion of fibrinogen to a fibrin clot. Their participation in this cascade is initiated by changes in the primary or conformational structure of the proenzyme which converts it to an active proteolytic enzyme. This change is termed "activation" of the proenzyme. For the sake of brevity, "blood clotting enzymes" shall include both the enzymatically nonfunctional proenzymes as well as their enzymatically active forms obtained by activation. Similarly, recitation of factor designations or names as used herein shall be construed to include both forms of the enzymes, e.g., "factor X" shall include both activated as well as unactivated factor X and mixtures thereof. From time to time the abbreviation "F" will be used for "factor".

Each of the blood clotting enzymes has its own specificity and performs an established task in the clotting mechanism. For example, activated factor IX hydrolyzes factor X in the presence of calcium and factor VIII, a protein cofactor, to produce activated factor X. Thrombin (activated prothrombin) cleaves fibrinogen, a protein substrate, to yield fibrin monomers which eventually form a clot.

Factors VII (proconvertin), IX (plasma thromboplastin antecedent) and IX (Christmas factor) are all beta globulins. The molecular weight of factors VII and IX are about 35,000 and 50,000 respectively. Factor X, also called Stuart-Prower factor, is an 87,000 molecular weight alpha globulin. Prothrombin (factor II) is a glycoprotein having a molecular weight of about 68,000. Hageman factor (factor XII) is also a glycoprotein, but its molecular weight is about 82,000.

These factors all have in common their biological role as proenzymes and clotting enzymes in the clotting of blood, a role not shared by other plasma proteins such as antithrombin III, albumin, antihemophilic factor (factor VIII), gamma globulin or fibrinogen. Plasminogen is not a blood clotting proenzyme as that term is used herein because its active form does not participate in the generation of the clot but instead digests fibrin in an existing clot.

Blood clotting enzymes are prepared commercially by known methods from large pools of individual blood plasma donations. All plasma units utilized in their manufacture are tested for the presence of hepatitis B surface antigen using test systems licensed for that purpose. These immunological tests, however, are not sufficiently sensitive to detect all potentially infectious units of hepatitis B. In addition, hepatitis virus may be concentrated during the fractionation procedure. Thus, the small amount of undetectable virus that may be contained in a large plasma pool may become significantly infective when it is concentrated several fold.

The development of specific diagnostic test for hepatitis A and hepatitis B has made it possible to identify a third type of viral hepatitis that is apparently unrelated immunologically to either of the first two. The transmissible agent, non-A, non-B hepatitis, has been confirmed by transmission of the disease to chimpanzees by exposure to pathological material. There are several lines of evidence pointing to more than one non-A, non-B hepatitis virus. These include cases with sequential episodes of apparent acute non-A, non-B hepatitis, variability in epidemiology and clinical syndromes including incubation periods.

Specifically in the case of blood clotting enzymes, hepatitis transmission via infusion of the products remains a problem even where the source plasma has been screened for hepatitis B. (Roberts et al., "Thrombos. Diathes. Haemorrh. [Stuttg.] 33: 610–616 [1975]). Furthermore, it is conceivable that adventitious viruses other than those responsible for hepatitis could contaminate the preparations. Thus a need exists for a process that will inactivate all viruses, including hepatitis, that may be found in these preparations.

Scattered reports exist of inactivating hepatitis virus in plasma or solutions of blood plasma fractions by heating the liquid plasma or fraction. Murray in "The New York Academy of Medicine" 31(5): 341-358 (1955) reports inactivating icterogenic activity in plasma by heating at 60° C. for ten hours. This procedure has long been used to inactivate hepatitis in albumin and plasma protein fraction (PPF) solutions.

Belgian Pat. No. 844,566 discloses heating liquid plasma or serum for ½-4 hours at 50°-60° C. to kill hepatitis virus, followed by fractionating the plasma or serum to obtain immune globulin G.

West German Offenlegungschrift No. 29 16 711 discloses stabilizing plasminogen, prothrombin, antithrombin III and factors II and VIII against heat in aqueous solution by adding an amino acid and a monosaccharide oligosaccharide or sugar alcohol to the solution. The solutions were heated for 1 minute to 48 hours at from 30 to 100° C. to inactivate hepatitis virus.

All of the foregoing techniques are disadvantageous. While the viruses may be inactivated, certain therapeutic proteins are also inactivated because they are thermally unstable in aqueous solution. Thus a reduction in the infectiousness of such protein compositions is accompanied by losses in the biological activity of the protein.

It is known to inactivate canine hepatitis virus in dry fibrinogen or albumin preparations by heating the preparations for 10 hours at 60° C. (Rozenberg et al. XII International Congress on Blood Transfusion, Abstracts p. 473–474 [1969]).

SUMMARY OF THE INVENTION

It has now been found that viruses, particularly hepatitis viruses, present in compositions containing blood clotting enzymes or mixtures of the enzymes may be inactivated without substantially affecting the activity of the enzymes by heating the enzymes in the dry state until the viruses are inactivated. The resulting novel compositions contain noninfectious virus and are substantially free of infectious virus and denatured blood clotting enzymes. The preferred compositions are substantially free of infectious hepatitis virus. The inactivation is monitored by the use of a dry biological indicator comprising protein and a predetermined viral titer.

BRIEF DESCRIPTION OF THE DRAWING

The FIGURE is a plot of the relationship between sindbis virus and prothrombin complex inactivation on the one hand and temperature and time on the other. In the dry state, the rate of viral inactivation far exceeds that of the clotting factors, as shown by a comparison of the dashed inactivation lines, representing clotting factor inactivation, and the solid lines, representing viral inactivation. In particular, the FIGURE demonstrates that a sindbis virus population in prothrombin complex can be effectively inactivated in less than 31 hours, with virtually no concommitant loss in enzyme activity.

DETAILED DESCRIPTION OF THE INVENTION

The clotting factor enzymes to be treated in accordance with this invention may be manufactured from blood plasma in any known fashion. Suitable examples of such methods are disclosed in U.S. Pat. No. 3,560,475. Other methods will be apparent to the ordinary artisan.

The enzymes should be purified about from 3 to 50 fold over their concentration in normal human plasma and contain less than about one percent the amount of protein in normal human plasma. The degree of purification is not critical. However, less pure product will have a relatively low therapeutic utility because only limited volumes of protein solution can be administered to a patient, and this volume may not contain the desired amount of clotting factors. On the other hand, more extensive purification may be unnecessarily costly in providing the desired therapeutic utility. Ordinarily the products will be substantially free of plasminogen, plasmin, gamma globulin, antihemophilic factor, albumin and fibrinogen. Occasionally, albumin may be present in about from 1 to 3 percent by weight. Optimally, the enzymes are sufficiently pure as to be substantially free of reducing monosaccharides from the starting plasma, in particular glucose.

The enzyme compositions may contain one or more conventional enzyme stabilizers such as amino acids, innocuous proteins, nonreducing monosaccharides, oligosaccharides and sugar alcohols. Representative stabilizers include albumin, glycine, proline, mannitol and sorbitol. If the compositions are to be used therapeutically one must use physiologically-acceptable stabilizers in physiologically-acceptable amounts. Generally, the stabilizers are present in amounts ranging from about 0.5% to 3% by weight. The stabilizers also accelerate dissolution of the lyophilized compositions and enhance the clarity of the solutions so formed. However, it is preferred that the compositions to be treated contain no stabilizers; generally, the stabilizers are unnecessary because the enzymes alone exhibit remarkable stability in the dry state. Thus the compositions may contain less than 1.0 mole/l of amino acid, preferably less than about 0.75 mole/l and less than 20% w/w of saccharide or sugar alcohol, preferably less than about 5% saccharide or sugar alcohol.

The pH of compositions which may be treated according to the process described herein will range from about 6.0 to 8.0, and is preferably about from pH 6.5 to 7.5. The clotting enzymes prothrombin, Hageman factor and factors XI, VII, IX and X may be further purified so as to be substantially free from one another. When an enzyme composition is said to be substantially free of another enzyme as that language is used herein, the contaminant enzyme is ordinarily present in quantities less than about 2% by weight based on the amount of the entire composition, or less than about 10% based on the weight of the predominant enzyme. Factor IX is commonly prepared as such an isolate by known methods, e.g., by affinity chromatography on heparin agarose, so that the concentration of factor IX is about from 25 to 50 times that of either factor X or thrombin. Such factor IX preparations usually contain about from 20–120 units of factor IX/ml. Prothrombin also may be removed by known methods. Such compositions substantially free of prothrombin may be used in the method herein. Other techniques are well known for separating the various blood clotting enzymes.

Four of the blood clotting enzymes are found in two widely used therapeutic products, prothrombin complex and activated prothrombin complex. Prothrombin complex ordinarily contains prothrombin and factors VII, IX and X in about the following unit ranges per ml, respectively: 1–10, 37–190, 15–142 and 1–30, preferably 3.6–8.9, 37–122, 20–81 and 1–25 respectively.

Activated prothrombin complex may be prepared in known fashion. For example, see Eibl et al., U.S. Pat. No. 4,160,025. Such compositions may be essentially free from unactivated clotting enzymes, but in the usual situation the activated enzymes are found in admixture with the proenzymes. It is surprising that not only is the biological activity of both unactivated and activated clotting enzymes preserved by the method disclosed herein, but that the proenzymes are not activated by the heat treatment.

Activated prothrombin complex (PCC) will generally contain the following ranges of activity (activated factor activity is represented by the postscript "a").

TABLE 1

ACTIVATED PCC CLOTTING FACTOR LEVELS
Range in units/ml

| Factor | Typical | Preferred | Most Preferred |
|---|---|---|---|
| II | 1–10 | 3.6–8.9 | 3.6–5.9 |
| VII | 37–190 | 37–122 | 39–88 |
| VIIa | 8–80 | 25–78 | 25–60 |
| IX | 15–112 | 20–81 | 50–80 |
| IX Precursor | 0–30 | 5–20 | 5–12 |
| X | 1–30 | 1–25 | 1–13 |
| Xa* | 1–20 | 1–10 | 4–10 |
| Xa+ | 1–10 | 1–8 | 1–5 |
| Thrombin | 0.003 | 0.002 | 0.001 |

*as determined by clotting assay (infra)
+ as determined by chromogenic assay (infra)

Obviously the ranges for each of these factors expressed in units/ml will depend upon the reconstitution volume of the activated PCC, which may be varied depending upon the intended use for the product. The ranges given above are for activated PCC which is diluted or reconstituted for direct administration to a patient. Unless otherwise stated, the ranges for factor Xa are those determined by the clotting method described below.

A preferred composition comprises, in units/ml, about from 20 to 112 units of F-IX and from 0 to about 30 units of F-IX precursor.

Another preferred composition comprises, in units/ml, about from 37 to 190 units of F-VII and about from 25 to 80 units of F-VIIa.

A further preferred composition comprises, in units/ml, about from 1 to 13 units of F-X and about from 4 to 10 units of F-Xa.

Also useful are products comprising factors VIIa, IXa and Xa and having a non-activated partial thromboplastin time of about from 27 to 70 seconds.

The analytical methods for determining factors XI, XII, II, VII, IX, X, Xa, IX precursor, VIIa and thrombin are conventional and well known to those skilled in the art. All of the assays specifically used with the compositions described herein have certain features in common, unless otherwise specified. First, each assay includes making duplicate serial dilutions of test sample and a standard having an assigned potency of 1 unit/ml. The concentration in units/ml of the test sample may then be calculated by averaging the duplicates, plotting the results obtained with the standards against their respective percent concentrations as established by their previous serial dilution, reading the percent concentrations in the diluted test samples from the plot, correcting the test sample concentrations for the serial dilutions which were made, averaging the test sample percent concentrations and dividing the average by 100 to arrive at the units/ml of the assayed factor.

Second, unless otherwise indicated all assays are conducted at 37° C. and all reagents are prewarmed to that temperature.

Third, assay standards in units/ml are based on lyophilized normal human plasma, frozen normal human plasma or international (BoB or WHO) standards intended to represent normal clotting factor activities. The lyophilized normal human plasma is standardized against three separate freshly drawn pools of normal human plasma. Each pool is prepared by collecting venous blood from 10 fasting, normal donors who are not taking oral contraceptives, anti-inflammatory drugs or arthritis medication. The donors must also have a prothrombin time of 11–15 seconds, an activated partial thromboplastin time of 30–45 seconds and a fibrinogen level of 200–400 mg/dl. The blood is collected into 3.8% sodium citrate at a ratio of 9 volumes of blood to 1 of anticoagulant, mixed, centrifuged at 1000 RCF for 15 minutes, after which equal volumes of each plasma supernatant are pooled. The plasma is assayed within one hour. The average potency of the three pools for each total factor assayed below is arbitrarily set at 1 unit/ml.

The frozen normal human plasma is prepared in identical fashion to any one of the three freshly drawn pools described above, except that the pool is distributed in 1 ml volumes into plastic vials and frozen at $-70°$ C. The frozen pools are used within 60 days. Each frozen pool is considered to contain 1 unit of each total factor/ml. Hereinafter, plasma which contains standard unitage as established by either of the two foregoing techniques will be referred to as reference or standard plasma.

Fourth, the factor deficient plasma used in some assays is plasma obtained from donors that are congenitally deficient in the particular factor, i.e., who have a factor potency of less than about 5% of that present in normal pooled plasma.

Fifth, the F-IX assays detect total and precursor F-IX. This means that the total F-IX assay measures the sum of activated and unactivated F-IX activity, while the F-IX precursor assay substantially excludes the activated material. Therefore F-IXa may be estimated by subtracting the precursor activity from the total F-IX. It should be noted that the remaining analytical methods, i.e., for factors II, VII, X, XI and XII, all measure the sum of active and proenzyme factor. However, in the interests of brevity the designation "total" will not be applied to these assays. On the other hand, and in contrast to the F-IX methods, the thrombin, VIIa and Xa methods are direct assays of the active factors.

Thrombin is determined by the following technique. A bovine thrombin standard, which has been standardized against the NIH Thrombin Standard, lot B-3, is diluted in normal saline to 0.001, 0.002, 0.003, 0.005 and 0.010 u/ml. 2.0 ml of this diluted standard is added to 0.5 ml of fibrinogen substrate. The mixture is incubated at 28° C. The reaction tubes are checked every 2 minutes. First fibrin strand appearance is taken as the end point. The test sample is assayed identically, but with no dilution. Thus, 2.0 ml of the reconstituted test sample is added to 0.5 ml of the fibrinogen substrate and end point formation is observed at 2 minute intervals. The clotting times of the test sample are compared with the clotting times of the thrombin standard. The calculations are conducted as generally described above.

Factor Xa is determined by a modification of the method of Yin et al., "J. Lab. Clin. Med." 81: 298 (1973). All reagents, including the reference standard, are commercially available from the Sigma Chemical Company. Test samples are serially diluted in duplicate into the buffer employed by Yin et al. at dilutions of 1:8, 1:16 and 1:32, or higher (expressed in parts of sample to parts of buffer) until the clotting time of that dilution is longer than the clotting time of the factor Xa standard at a concentration of 0.01 units/ml.

Standard factor Xa is initially diluted 1:4 into the same buffer, followed by serial dilutions in duplicate to 1:64. A 1:4 dilution of standard F-Xa is taken as 1 unit F-Xa/ml. Standard F-Xa is defined as that which will produce an average clotting time of 14 seconds at 1:2 dilution in the assay described herein. 0.1 ml of each final dilution is pipetted into a fibrometer cup, followed by 0.1 ml of 0.025M $CaCl_2$ and 0.2 ml of a bovine plasma-rabbit cephalin solution to initiate clotting. The clotting time for each tube is determined and the F-Xa activity calculated as described above.

F-Xa may also be determined by a chromogenic assay as an alternative to the clotting method described in the preceding paragraph. Unless otherwise stated by designation of the assay results as "chromogenic" it will be assumed that the F-Xa was determined by the clotting method. The chromogenic assay is essentially disclosed by Kosow in "Thrombosis Research" 1: 565–573 (1976). It employs a synthetic substrate which is specifically hydrolyzed by F-Xa to yield a chromogen detectable by its absorption of light at 405 nm. The substrate, S-2222, is commercially available from Ortho Diagnostics, Inc. Standard F-Xa is available from the Sigma Chemical Co., but is diluted 1:4 into 0.05M Tris buffer at pH 8.3 containing 1.33% NaCl by weight before use. A 1:4 dilution of a standard containing 0.5 unit F-Xa/ml should exhibit an average optical density at 405 nm of 0.260 in the assay. In the practice of the assay, samples and diluted standard are serially diluted into the Tris buffer. 0.4 ml of each dilution is pipetted into a glass test tube, followed by 0.075 ml of a solution containing 0.5M $CaCl_2$ and 0.1M NaCl and, after 1 minute, 0.5 ml of an S-2222 solution in 0.05M Tris buffer at pH 8.3 containing 0.9% NaCl by weight. 0.1 ml of 50% acetic acid is added after 3 minutes to stop the reaction and the absorbance is read against a buffer blank at 405 nm. The calculations are conducted as generally described above.

Factor X is determined by a modification of the Bachmann et al. method described in "Thromb. et Diath." 2: 24 (1958) except that factor X deficient plasma is used in place of Seitz filtered ox plasma, a fibrometer is used for end point detection and the diluting fluid is veronal buffer containing sodium chloride and sodium citrate as described by Proctor et al., "Am. J. Clin. Path." 36(3): 214(1961). Russell's viper venom and cephalin were obtained from Burroughs Wellcome & Co. and the Hyland Division of Travenol Laboratories, Inc., respectively. The calculations are made as generally described above.

Prothrombin (factor II) is assayed by the following technique. 0.1 ml of factor II deficient plasma prepared by the method of Pechet in Tocantins, Ed., *Blood Coagulation, Hemorrhage and Thrombosis*, volume 1, pp 144–148 (1964) is distributed into each of eight test tubes. A 100% reference plasma is prepared by diluting reference plasma 1:10 into 1.72% imidazole weight/volume buffer at pH 7.3. This reference plasma is then further diluted 1:5, 1:10, 1:20 and 1:40 into the same buffer. Duplicate 0.1 ml aliquots of each dilution are pipetted into the test tubes containing factor II deficient substrate. Immediately after pipetting the reference plasma into each duplicate set of test tubes, 0.2 ml of rabbit brain thromboplastin lyophilized with $CaCl_2$ is added to each test tube by means of a plastic-tipped pipette. After mixing for 15 seconds each tube is tilted back and forth once per second over a light source and the time that elapses before final gel formation is recorded. The foregoing procedure is repeated with the test sample, except that a 1:100 dilution into imidazole buffer is made before the 1:5, 1:10, 1:20 and 1:40 dilutions. The data is handled in the same fashion as discussed above.

F-IX is determined by the following procedure, essentially that of Proctor et al., op cit. A minimum 1:20 predilution of the activated PCC test sample is prepared in normal saline. Reference plasma is not prediluted. Then duplicate 1:5, 1:10, 1:20 and 1:40 dilutions in barbital buffered saline of test sample and reference plasma are pipetted into test tubes already containing 0.1 ml of partial thromboplastin-kaolin described in the Proctor et al. procedure and 0.1 ml of F-IX congenitally deficient plasma having less than 5% of normal F-IX activity. After 3 minutes, 0.1 ml of 0.03M $CaCl_2$ is mixed with the contents of each test tube, incubated for 30 seconds and then each test tube is tilted at less than once per second in front of a light source until final gel formation. The time from $CaCl_2$ addition to gel formation is recorded and that data treated as generally described above.

F-IX precursor is assayed exactly as set forth above for total F-IX except that the initial minimum 1:20 dilutions of test sample are made up in the F-IX deficient substrate rather than normal saline.

Factor VII is determined according to Esnouf et al. in Bang et al., Ed., "Thrombosis and Bleeding Disorders, Theory and Methods", pp 197–198, (1971) except that the clotting point was determined with a Clotek ® device and the diluting fluid was that described by Proctor et al. op cit.

Factor VIIa is assayed by first adsorbing the sample with a benzamidine-Sepharose affinity matrix. The benzamidine-Sepharose matrix is a well known affinity gel disclosed, for example, by Schmer, "Z. Physiol. Chem." 353: 810–814 (1972). The non-adsorbed fraction is removed from the matrix by washing with 0.1M $NaHCO_3$, pH 7.8. Then, the same buffer containing 0.5M NaCl and 0.3M benzamidine HCl is used to remove the fraction containing VIIa. Assay of the latter fraction for VIIa is accomplished with the same assay and reference which are used for F-VII.

The assay for factor XI is described by Rappaport et al. in "J. Lab. Clin. Med." 57: 771 (1961), except that the $CaCl_2$ solution is 0.03M, a cephalin-kaolin mixture commercially available from the Hyland Division of Travenol Laboratories, Inc. was employed and the clotting point was determined with a Clotek ® device.

Factor XII is determined in essentially the same way as factor XI. However, here a factor XII deficient plasma is used and the assay is only conducted in contact with plastic ware.

The activated PCC treated by the method of this invention are characterized overall by their ability to correct the clotting time of factor-deficient or inhibited plasma, and specifically by the amounts or activities of individual clotting factors, overall procoagulant activity as reflected in the nonactivated partial thromboplastin time, substantial freedom from thrombin activity and substances which induce an immune response to factor VIII in treated patients and, optimally, about 0.1 to 3 units antithrombin III/ml in the final product. Both activated and inactivated PCC may contain greater than about 1 unit of heparin/ml, usually about from 1 to 3 units/ml.

The enzyme compositions and biological indicators as further described herein must be heat treated in the dry state. This means that they should contain less than about 5% water by weight, whether or not a liquid, aprotic solvent is present. The compositions may be powder, cake or other suitable form. While lyophilization of the compositions under ordinary conditions will generally produce a product having a weight percent of water lower than about 3.5%, it is preferred to lyophilize sufficiently to produce a composition having less than about 1% water by weight.

The blood plasma clotting enzymes are optimally treated after ordinary, conventional packaging in final containers such as glass vials, i.e., after being dispensed into the containers as sterile filtered (for cellular organisms) aqueous solutions, lyophilized and sealed. It is preferred to heat treat finally packaged, sealed containers. Viral inactivation in such containers is followed by the use of biological indicators as described below.

It is not necessary to provide any special atmosphere over the enzymes to be heat treated. Air is most economical because it obviates the need for any special packaging steps. However, best results are visually achieved with a vacuum or an oxygen-free atmosphere after a dry nitrogen sweep to reduce residual moisture and oxygen.

Optimal conditions for the production of a composition which is substantially free of infectious virus, or for simply reducing the viral titer, will depend upon the nature of the blood clotting product which is being treated. For example, product variations which will affect the comparative inactivation rates of enzymes and viruses include the concentrations and types of salts in the compositions, the virus type, the extent of viral contamination, the relative proportions of the enzymes to other proteins, the retained water content of the compositions, the pH of the factor solution before drying and the presence in the solution of additives such as monosaccharides, antioxidants and the like. Since the product to be treated is often quite variable, being derived from a biological source, it is preferred to vary the inactivation conditions to suit the product characteristics. The conditions which are most conveniently varied to optimize viral inactivation while preserving enzyme activity are the time and temperature of the heat treatment. However, this is not to exclude the possibility of also modifying the product characteristics to aid in the process. For example, the enzyme solution can be given a preliminary purification, e.g., adsorption of some of the contaminant viruses onto insolubilized antibody specific for the virus, thus reducing the extent of heat treatment required to inactivate the viruses.

The inactivation temperature is directly proportional to the rate of inactivation of virus and enzyme. Thus, the higher the temperature, the more rapid the inactivation of both the virus and clotting factor enzyme. The method herein relies on the phenomenon that the comparative inactivation rates of virus and enzyme diverge, so that it is possible to inactivate the virus without substantially inactivating the clotting factor enzyme. Thus the optimal temperature may be expressed functionally as that at which the rates are most divergent, i.e., where the difference in the slope of a plot of viral inactivation against time and the slope of a plot of enzyme inactivation against time is greatest. However, it may be desirable to employ temperatures higher than the point of greatest divergence so as to reduce the net heat treatment time. Ordinarily, a temperature of about from 40° to 80° C. is satisfactory, with about from 50° to 60° C. being preferred and about 60° C. being optimal with most enzyme compositions.

The heat is provided by any suitable heating device, e.g., convection oven, infrared irradiation or sand or water bath. A water bath is preferred.

The time needed for viral inactivation at the above temperatures is generally about from 5 to 200 hours, usually about from 10 to 40 hours. While a standardized time period can be used for uniform lots of clotting enzyme, it is preferable to assay the composition for viral biological activity to determine whether or not the inactivation is complete. The virus to be assayed may be the one which is suspected to contaminate the composition, e.g., hepatitis B or non-A, non-B hepatitis, or the virus may be one which has been preselected for use in a biological indicator. A biological indicator acts as a product surrogate in that the inanimate portions are designed to mimic the product while a living organism is selected to mimic the expected contaminants.

Biological indicators heretofor have been articles containing sterilant resistant cellular organisms or spores of such organisms. These known biological indicators are most commonly available as dry, bibulous strips impregnated with the heat resistant spores of certain bacteria, e.g., bacillus, which in turn are encased in packages which are permeable to the sterilizing agent, e.g., steam. The biological indicator herein provided is a dry composition comprising blood protein and a predetermined titer of an infectious virus which is not a candidate for in serum hepatitis infection. This means that etiological agents for viral hepatitis may be used but that they should not be those which are transmissible by infusion of plasma from an infected donor. For example, Hepatitis B is a serum hepatitis agent. Ideally, the virus will not be a candidate for hepatitis infection at all.

The blood protein mimics the effect of the protein in the product which is to undergo the virus inactivation process. Thus the indicator protein may be the same or different from the proteins in the product to be treated, either in terms of identity, proportion or species of origin. Thus a variety of commonly available blood plasma proteins may be employed, e.g. immune globulin, albumin, antihemophilic factor, antithrombin III, clotting enzymes and mixtures thereof. If is preferred that the protein be substantially free of albumin and fibrinogen. Where AHF is used the composition will contain greater than about 35 International Units/gm of protein, up to about 200 Units/gm. In a preferred embodiment the indicator protein composition is substantially the same as that in the product to be treated. In fact, suitable indicators may be prepared from aliquots of each plasma protein lot to be treated. The protein is preferably human, but bovine or porcine sources may also be used.

The virus is preferably not normally infectious for humans, thus reducing containment costs. However, for the safety of laboratory workers and to ensure integrity of treated product it is important that the virus not be a candidate or known agent responsible for hepatitis infection upon infusion into humans. Such viruses are hazardous and their introduction into the plasma fraction manufacturing environment should be avoided. The concentration of virus will range about from 3 to 80 $\log_{10}$ plaque-forming units in about from 0.01 to 1 gram of protein.

The indicators are ordinarily made by suspending the virus in an aqueous solution of the proteins, filling into 10 or 30 ml containers of glass or plastic, lyophilizing and sealing under vacuum or an inert gas such as nitrogen. The compositions are water soluble upon reconstitution.

They are used by exposing the indicator to the same conditions as are used to inactivate the virus in the treated composition and then assaying for the virus, if any, which remains unactivated in the biological indicator. It is preferred to place biological indicators in among the product vials and then to heat treat; this helps ensure that the inactivation conditions are substantially identical.

Suitable viruses for use in the biological indicators include bacterial, plant and animal viruses. The animal viruses are preferably not normally infectious for humans for safety reasons. Also, the virus ideally should not be infectious for the donor species of the protein used in the biological indicator. The reason for this is that such protein could be contaminated with antibody to the virus as a result of prior infection or vaccination of the donor, and the antibody may interfere with viral cultivation. The best biological indicators for the purposes herein use viruses which are highly stable thermally. In this respect the bacterial viruses, known as bacteriophages, are excellent choices. Finally, the virus should be easily cultivated. Most plant and animal viruses meet this preferred criterion, but bacteriophage is most readily and inexpensively cultured.

Exemplary viruses include picornaviruses such as encephalomyocarditis virus (EMC), mouse encephalomyelitis virus, simian enterovirus and bovine enterovirus; togaviruses including sindbis, semliki forest virus, western equine encephalitis virus and yellow fever virus; retroviruses such as rous sarcoma virus; paramyxoviruses such as newcastle disease virus; papoviruses including polyoma virus and simial virus 40; herpes viruses such as herpes simplex, pseudorabies virus and mareks disease virus; members of the adenovirus family such as infectious canine hepatitis and adeno virus; and bacteriophage such as R17, lamda, T1, T2, T4, T7 and Phi X 174. Mixtures of the viruses may also be used.

Suitable methods for determining viruses in the treated product or in biological indicators are quite conventional and will be apparent to the artisan. One such method is known as the plaque-forming test. In this method, dilutions of test sample in a physiological diluent are contacted with an immobilized layer of living, susceptible cells, time is allowed for the viruses to adsorb to the cells, the cells are overlaid with a growth medium gel, and other conditions are set to otherwise optimize survival of the cell culture. Viruses that infect and multiply within the cells are localized by the agar overlay. Virus spread is from the primary infected cells to adjacent cells producing a circular area of cellular degeneration of foci called a plaque. These foci are usually visualized by staining the monolayer with a vital stain, neutral red. The foci of infected cells fail to take up the vital stain and thus appear as clear areas against a colored background. Accordingly, the number of plaques is a measure of the infectivity of the test sample.

Other assays that may be employed include in vivo tests for infectivity towards susceptible hosts. Such methods are well known. Hepatitis B must be assayed in this manner because it has not been possible heretofore to culture the virus in vitro. The usual procedure is to inoculate hepatitis-B antibody negative chimpanzees or marmosets with the samples to be tested, incubate for several weeks, and then observe for clinical and serological evidence of hepatitis-B infection.

Immune assays for normal viral antigens in treated samples will yield reasonably conclusive results only if no antigen is detectable and, as noted above, the immune assay is sufficiently sensitive. If both requirements are met, the treatment has been sufficiently rigorous to completely denature the viral epitopic sites. It is generally safe to assume that such treatment has also rendered the viruses biologically inactive, and thus noninfectious. However, determining the point at which viral inactivation has occurred by the use of such assays is not preferred because the conditions needed to denature antigens will be far more severe in most cases than those necessary to biologically inactivate the virus. Thus unnecessary losses in product will occur before the sample can be verified as noninfectious.

A particularly noteworthy feature of the process herein is that all hepatitis virus can be inactivated by heat treatment, but without a significant reduction in enzyme activity. This includes hepatitis A, hepatitis B and non-A, non-B hepatitis. These viruses are the principal, known contaminants of therapeutic blood clotting enzyme compositions. The advantage of the present method is that the particular identity of the viruses described above for use in biological indicators, as well as the in vivo activity of the above hepatitis viruses, can be destroyed without a simultaneous comparable reduction in enzyme activity. However, the method described herein has broad applicability to all viruses present in blood clotting enzyme compositions.

The compositions produced by the novel method herein are unique in that while they are substantially free of biologically infectious virus, they do contain the residue of the heat-treated, biologically noninfectious virus. For example, hepatitis-contaminated enzyme compositions which are rendered noninfectious in vivo contain residues which are in part still immunologically cross-reactive with the infectious virus, as may be detectable under the state-of-the-art by immunological competitive displacement in conventional assays for the active virus.

Further, the compositions are substantially free of denatured blood clotting enzymes. A denatured blood clotting enzyme is generally defined as that in which the enzyme activity is irreversibly destroyed, whether by heating in aqueous solution or by other techniques used to inactivate the virus. The composition herein generally will contain no more than about 10 mole percent of denatured enzyme based on the total moles of denatured and active enzyme. The compositions preferably contain less than about 5 mole percent of denatured enzyme. The denatured enzyme can be detected by immunoassay using conventional techniques.

The enzyme composition produced by the method herein may be reconstituted to therapeutically effective concentrations and infused into patients. Such compositions are sterile. However, the compositions need not be sterile if they are to be used as reagents in diagnostic tests. For example, a composition containing a given clotting enzyme may function as a standard or control in an assay for that clotting enzyme. An antimicrobial agent such as an azide is preferably included with the composition since such compositions are commonly reconstituted and stored for usage over a period of time during which bacteria could grow and adversely affect the reagent. Alternatively, diagnostic reagents may be sterilized by sterile filtration and packaging.

Whole or defibrinated plasma may be made in the same fashion as the blood clotting enzyme, particularly for use as hepatitis-free controls and standards, if the reducing sugar content of the plasma or component is lowered to a level which is relatively nondestructive towards enzymes such as the dehydrogenases and creatine phospholinase. The sugars can be added to the plasma after the heat treatment if necessary.

The invention will be more fully understood by reference to the following examples.

EXAMPLE 1

This example demonstrates the thermal stability of dry prothrombin complex. This product is substantially non-activated. 30 ml sealed vials of lyophilized prothrombin complex from each of two commercial prothrombin complex lots prepared essentially by the method of Fekete et al., U.S. Pat. No. 3,560,475 were heated in triplicate for the times and temperatures described in Table 2. The prothrombin complex clotting factors, activated factor X(Xa), activated factor II (thrombin) and pH were each assayed in accordance with conventional methods as described above. The Kingdon time at a sample dilution of 1:100 was determined in accordance with Pepper et al., "British Journal of Hematology" 36:573(1977) or Kingdon et al., Abstract #86 of the meeting of the American Society of Hematology, Atlanta (1974). This assay is also known as the non-activated partial thromboplastin time test. Proteolytic activity was assayed using two synthetic, chromogenic protease substrates, S-2160 (N-benzoyl-phenylalanyl-valyl-argininyl-p-nitroanilide HCE) and S-2238 (D-phenyalanyl-pipecolyl-argininyl-p-nitroanilide HCE) available from Ortho Diagnostics. The results are set forth in Table 2 below.

TABLE 2

CHARACTERISTICS OF PROENZYME CLOTTING FACTORS IN HEATED PROTHROMBIN COMPLEX

| | | 60° C. | | 70° C. | |
|---|---|---|---|---|---|
| | 5° C. | 4 days | 7 days | 4 days | 7 days |
| Lot 581M133 | | | | | |
| F-Xa (u/ml) | 0.1 | 0.1 | 0.2 | 0.1 | 0.2 |
| Kingdon Time (Sec.) | 195 | 175 | 149 | 184 | 177 |
| Thrombin | 0.001 | 0.001 | 0.001 | 0.001 | 0.001 |
| Proteolytic Activity | | | | | |
| Substrate S-2160 | 0.2 | ND* | 0.2 | ND | 0.2 |
| Substrate S-2238 | 0.07 | ND | 0.10 | ND | 0.12 |
| pH | 7.0 | 7.0 | 7.0 | 7.0 | 7.0 |
| | | Percent Activity Remaining | | | |
| F-II | 100 | 91 | 100 | 88 | 81 |
| F-VII | 100 | 111 | 102 | 92 | 78 |
| F-IX | 100 | 89 | 84 | 81 | 70 |
| F-X | 100 | 94 | 83 | 90 | 78 |
| Lot 581M164 | | | | | |
| F-Xa (u/ml) | 0.2 | 0.2 | 0.1 | 0.2 | 0.2 |
| Kingdon Time (Sec.) | 170 | 195 | 172 | 154 | 137 |
| Thrombin (u/ml) | 0.001 | 0.001 | 0.001 | 0.001 | 0.001 |
| Proteolytic Activity | | | | | |
| Substrate S-2160 | 0.2 | 0.2 | 0.2 | 0.2 | 0.2 |
| Substrate S-2238 | 0.07 | 0.06 | 0.05 | 0.07 | 0.06 |
| pH | 7.0 | 7.0 | 6.9 | 6.9 | 7.0 |
| | | Percent Activity Remaining | | | |
| F-II | 100 | 97 | 90 | 89 | 84 |
| F-VII | 100 | 93 | 102 | 97 | 94 |
| F-IX | 100 | 92 | 95 | 76 | 88 |
| F-X | 100 | 104 | 90 | 79 | 80 |

*ND = Not Done

The average percent activity remaining for the four unactivated clotting factors was calculated at 4 days and 7 days for each temperature and then plotted in the FIGURE as dashed lines.

EXAMPLE 2

This example deals with the thermal lability of virus in prothrombin complex. Suspensions of sindbis, encephalomyocarditis (EMC), polio type 1 and adeno type 5 viruses were each diluted into aliquots of prothrombin complex, dispensed in 1 ml aliquots into a 5 ml vial, lyophilized and sealed under vacuum. The vials were heated at 70° C. and 60° C. for up to 40 hours with sample vials being withdrawn at periodic intervals. The contents of the 5° C. control and heat treated vials were reconstituted with 1 ml sterile water and assayed for viral titer as described below. The control concentration of sindbis virus was about from 6 to 7 $\log_{10}$ of plaque forming units per reconstituted ml (PFU/ml), while EMC and polio virus were at about 4 $\log_{10}$ PFU/ml. The adenovirus concentration was about $4.5 \times \log_{10}$ tissue culture 50% infective dose (TCID-50)/ml.

The TCID designation may be explained as follows: In biological quantitation, the end point is usually taken as the dilution at which a certain proportion of the test system reacts or dies. The 100% end point is frequently used, However, its accuracy is greatly affected by small chance variations. A desirable end point is one representing a situation in which one-half of the test system reacts while the other one-half does not. The best method is to use large numbers of test systems at closely spaced dilutions near the value for 50% reaction and then interpolate a correct value. Negative logarithm of the $TCID_{50}$ end point titer=

$$\left(\begin{array}{c}\text{Negative logarithm of}\\ \text{the highest virus concentration used}\end{array}\right) -$$

$$\left[\left(\frac{\text{Sum of \% mortality at each dilution}}{100} - 0.5\right) \times \left(\begin{array}{c}\text{Logarithm}\\ \text{of}\\ \text{Dilution}\end{array}\right)\right]$$

The tissue culture 50% end point represents a viral titer that gives rise to cytopathic changes in 50% of the cells in an inoculated culture. In applying the above technique for determination of concentration, logrithmic dilutions are prepared in minimum essential medium plus 2% fetal calf serum. 0.2 ml of each dilution is added to replicate cultures of BGMK (Buffalo Green Monkey Kidney) cells in microtiter plates. The inoculated cultures are incubated at 36° C. under 5% $CO_2$ and observed microscopically over a period of 7 to 8 days. The percent mortality of cells in a culture at a given dilution is determined by observing for cellular degeneration, as evidenced by refractile cells. The TCID-50 can then be calculated as shown above.

The assay of EMC, polio virus and sindbis virus is obtained by preparing dilutions of viral suspension as described above. BGMK cell monolayers were prepared in 35 mm petri dishes. Viral adsorption to the cells was initiated by adding 0.2 ml of suspension to the monolayer. After 1 hour, the monolayer was overlaid with 2 ml of nutrient agar medium and incubated for 24–72 hours at 37° C. The plaques which formed were then made visible by staining the cells with neutral red at 1:2000 by weight in saline.

The results with sindbis virus were subjected to regression analysis with the method of least squares to allow the fitting of a linear line to the data and plotted in the FIGURE. As can be seen, the inactivation rate was much higher at 60° C. than at 47° C., while no change occurred in the 5° C. control. Similar results could be obtained with the other three viruses. A comparison of the results from Example 1 and 2 as plotted in the FIGURE shows that dry prothrombin complex enzymes are inactivated in heat at very low rates when compared to viruses. The greatest difference in the inactivation rates occurs at around 60° C. Here, only negligible losses in prothrombin complex have occurred at the time the virus is completely inactivated.

EXAMPLE III

This contemplated example is concerned with the inactivation of hepatitis B in activated and inactivated prothrombin complex. An aliquot of a production lot of commercially available prothrombin complex having a low titer of activated factors (Proplex ® fraction, Hyland Laboratories) was mixed with sufficient hepatitis B virus (obtained from the Hepatitis Branch of the Bureau of Biologics, Food and Drug Administration) to yield about 30,000 chimpanzee infectious doses/10 ml. An aliquot of activated prothrombin complex (Autoplex ®) concentrate, Hyland Laboratories) was similarly seeded with hepatitis B virus. The quantity of virus in the fractions was detectable at or near the sensitivity of third generation hepatitis B antigen ($HB_sAg$) detection systems. After the virus and prothrombin complex were mixed, the infected product was dispensed in 10 ml aliquots into vials, lyophilized, swept with dry nitrogen and sealed. Replicate vials containing contaminated unactivated and activated prothrombin complex were immersed for 72 hours in a water bath held at 60° C. to inactivate the virus. Untreated vials containing infected product were stored under regrigeration as controls.

Six chimpanzees (Pan troglodytes) were selected for the study. None has been used for hepatitis B research of any kind, been given blood or blood-based products, all were free of any clinical hepatitis symptoms and were negative for $HB_sAg$, antibody to $HB_sAG$ (anti-$HB_s$) and antibody to hepatitis core antigen (anti-$HB_c$) by licensed radioimmunoassay procedures. Base line values were established from eight weekly blood samples from each animal for alanine aminotransferase (ALT), aspartate aminotransferase (AST) and biweekly for complete blood count. The chimpanzees were deemed suitable once their health was established and it was determined that no intercurrent diseases were present.

The vials of hepatitis-B seeded product as prepared above were each reconstituted in sterile water to a volume of 10 ml. The reconstituted contents of each vial were intravenously injected into a chimpanzee. Two chimpanzees served as recipients for the two controls. The controls were reconstituted in 10 ml of sterile water and administered in the same fashion as the heat-treated products.

The chimpanzees were carefully quarantined and monitored for eight months for signs of hepatitis infection. $HB_sAg$, anti-$HB_s$, anti-$HB_c$, ALT, AST and antibody to hepatitis A virus were determined weekly and complete blood count made biweekly for 24 weeks after inoculation and then at weeks 28 and 32. The livers were biopsied at monthly intervals up to 6 months, and then at the thirty-second week. While the control animals developed hepatitis with the normal incubation span for the virus, the four chimpanzees injected with the heat-treated prothrombin complex and activated prothrombin complex were not infected.

EXAMPLE IV

This contemplated example demonstrates the inactivation of non-A, non-B infectious virus in prothrombin complex. The non-A, non-B hepatitis virus source used in this study was described by Bradley et al. "J. Med. Virology"3:253-269 (1979). The source was an antihemophilic factor lot (Hemofil ®) concentrate Lot 059D056AA) that had been demonstrated to cause hepatitis other than hepatitis A or B when administered intravenously in quantities of at least 3 ml. The source AHF lot was reconstituted in accordance with the manufacturer's instructions, diluted into a commercial lot of prothrombin complex (Proplex ® concentrate) in a ratio of 1 part source to 9 parts of prothrombin comlex, filled into vials in 10 ml aliquots, lyophilized, swept with dry nitrogen and sealed. Replicate vials were heated in the same fashion as in Example III, while a control was stored.

Three of the four chimpanzees that received heat-treated test materials in Example III and were thus free of hepatitis symptoms served as the experimental subjects in this study. The vials were reconstituted and injected as appropriate and the animals then quarantined and monitored for eight months. The tests and testing schedule were substantially the same as in Example III. The control animal also was tested for antibody titers to cytomegalovirus and Epstein-Barr virus when biochemical evidence of hepatitis became evident. The control animal was judged to have developed non-A, non-B hepatitis while neither of the recipients of heat-treated material were infected.

EXAMPLE V

Hepatitis A is inactivated in accordance with this contemplated example. The source for hepatitis A virus was a fecal sample from a patient in the acute phase of hepatitis A as determined by a commercially available radioimmunoassay for hepatitis A. The fecal sample was homogenized in 10 ml of saline and then centrifuged at 1,500×g to remove particulate matter. The supernatant was carefully decanted and centrifuged at 50,000×g in an ultracentrifuge until a viral pellet collected in the bottom of the centrifuge tube. The pellet was resuspended in saline to a titer of about 10 $\log_{10}$ particles/ml using immune electronmicroscopy. This suspension was diluted 1:5 into an aliquot of the commercial prothrombin complex lot used in previous examples dispensed in 10 ml volumes into vials, lyophilized, and sealed under vacuum.

The material was heat-treated and tested in chimpanzees in the same fashion as in Example IV. The heat-treated prothrombin complex was noninfectious.

EXAMPLE VI

This contemplated example discloses the manufacture and use of a biological indicator suitable for confirming the heat inactivation of viruses in blood plasma protein products. The representative plasma protein for use in the indicator was a commercially available AHF-containing composition having 15 International Units of AHF/ml and about 0.05 gram of protein per ml upon reconstitution according to the manufacturer's instructions. The composition contained fibrinogen and other unidentified plasma proteins in addition to AHF, but was free of detectable reducing sugar. T4 bacteriophage in sterile water was added to the dry, sterile AHF composition in sufficient quantity that the composition upon reconstitution contained about 6×$\log_{10}$ phage particles/ml. 1 ml of the composition was filled into ampules, lyophilized and the ampules were sealed under nitrogen. Then replicate ampules were heat-treated at 60° in tandem with a plurality of vials of factor IX for 90 hours, after which the contents of the ampules were dissolved in 1 ml of sterile water, diluted serially from 1:2 to 1:64 in sterile water and each dilution then overlaid onto petrie plates containing nutrient agan gel heavily seeded with E. coli bacteria. No plaques appeared at any dilution after 4-8 hours of incubation, thus demonstrating the inactivation of T4 phage in the AHF composition, and it was accordingly concluded that the heat treatment was successful at inactivating any endogenous viruses that might have been present in the factor IX preparation.

EXAMPLE VII

A stable, hepatitis-free blood plasma control was made in accordance with this contemplated example. 2 liter of a human blood plasma pool believed to be contaminated with hepatitis B virus was placed into a cellulose acetate bag and dialyzed against 20 liters of continuously exchanged saline. This treatment removed the reducing sugar (glucose and fructose) content of the plasma pool as well as other low molecular weight solutes such as amino acids, organic acids, bilirubin, creatine, creatinine, and uric acid. The dialyzed plasma was filtered to remove insoluble matter and then passed in a continuous stream into a moving bath of fluorocarbon refrigerant held at about −40° C. The plasma immediately froze into small spheres and was collected from the refrigerant. The refrigerant was allowed to drain from the frozen plasma, after which the plasma was lyophilized. The dry beads (about 130 g) were placed in a container, swept with nitrogen, the container sealed and immersed for 30 hours in a water bath maintained at 70° C. 1.4 g of powdered glucose was carefully blended with the dry plasma beads, the product filled into vials, weighed and sealed. The activity of diagnostically significant enzymes such as lactate dehydrogenase and creatine phospholinase was substantially preserved.

I claim:

1. A method for inactivating virus in a blood clotting enzyme composition suspected to contain such virus, which method for inactivating consists essentially of heating the composition in the dry state until the composition is substantially free of said virus in the infectious form and said blood clotting enzyme in the denatured form.

2. The method of claim 1 wherein the virus is hepatitis A, B or non-A, non-B.

3. The method of claim 2 wherein the composition contains up to about 5% water by weight.

4. The method of claim 3 wherein the composition contains about 1% water by weight.

5. The method of claim 2 wherein the enzyme is prothrombin.

6. The method of claim 2 wherein the enzyme is factor VII.

7. The method of claim 2 wherein the enzyme is factor IX.

8. The method of claim 2 wherein the enzyme is factor X.

9. The method of claim 2 wherein the enzyme is factor XI.

10. The method of claim 2 wherein the enzyme is Hageman factor.

11. The method of claim 2 wherein the enzyme is activated factor VII.

12. The method of claim 2 wherein the enzyme is activated factor IX.

13. The method of claim 2 wherein the enzyme is activated factor X.

14. The method of claim 2 wherein the enzyme is activated factor XI.

15. The method of claim 2 wherein the enzyme is activated Hageman factor.

16. The method of claim 2 wherein the composition consists essentially of factor IX.

17. The method of claim 2 wherein the composition is substantially free of thrombin.

18. The method of claim 2 wherein the composition is substantially free of plasminogen.

19. The method of claim 2 wherein the composition is substantially free of prothrombin.

20. The method of claim 2 wherein the composition is substantially free of fibrinogen.

21. The method of claim 2 wherein the composition is substantially free of antihemophilic factor.

22. The method of claim 2 wherein the composition is substantially free of albumin.

23. The method of claim 2 wherein the composition is substantially free of plasminogen.

24. The method of claim 2 wherein the composition is substantially free of factor XIII.

25. The method of claim 2 wherein the composition is substantially free of antithrombin III.

26. The method of claim 2 wherein the composition is substantially free of plasmin.

27. The method of claim 2 wherein the composition is substantially free of gamma globulin.

28. The method of claim 2 wherein the composition contains about from 1 to 3% albumin by weight.

29. The method of claim 2 wherein the composition includes a stabilizing amount of an amino acid.

30. The method of claim 29 wherein the amino acid is glycine or proline.

31. The method of claim 2 wherein the composition includes a stabilizing amount of a non-reducing monosaccharide, oligosaccharide or sugar alcohol.

32. The method of claim 31 wherein the composition includes a sugar alcohol.

33. The method of claim 31 wherein the sugar alcohol is mannitol or sorbitol.

34. The method of claim 2 wherein the composition contains less than 1.0 mole/l of amino acid and less than 20% w/w non-reducing monosaccharide, oligosaccharide or sugar alcohol.

35. The method of claim 2 wherein the composition has a pH of about from 6.0 to 8.0.

36. The method of claim 2 wherein the composition is activated prothrombin complex.

37. The method of claim 2 wherein the composition is substantially unactivated prothrombin complex.

38. The method of claim 2 wherein the composition contains factor IX and is substantially free of other blood clotting enzymes.

39. The method of claim 2 wherein the composition contains the following blood clotting enzymes, in units/ml: prothrombin, about from 1–10; total factor VII, about from 37–190; activated factor VII, about from 8–80; total factor IX, about from 15–112; factor IX precursor, about from 0–30; total factor X, about from 1–30; activated factor X, about from 1–20; and thrombin, less than about 0.003.

40. The method of claim 2 wherein the composition is filtered through a sterile filter to remove cellular microorganisms before the composition is heated.

41. The method of claim 2 wherein the composition is heated at about from 40 to 80° C.

42. The method of claim 41 wherein the composition is heated at about from 50 to 70° C.

43. The method of claim 41 wherein the composition is heated at about from 5 to 200 hours.

44. The method of claim 2 wherein the composition consists essentially of activated and unactivated factor VII.

45. The method of claim 1 wherein the composition is heated by infrared radiation, a convection oven, or a sand or water bath.

46. The method of claim 45 wherein the composition is heated by a water bath.

47. a method for inactivating hepatitis A virus in a blood clotting enzyme composition suspected to contain hepatitis A virus, which method for inactivating hepatitis A virus consists essentially of heating the composition in the dry state until the composition is substantially free of said virus in the infectious form and said blood clotting enzyme in the denatured form.

48. A method for inactivating hepatitis B virus in a blood clotting enzyme composition suspected to contain hepatitis B virus, which method for inactivating hepatitis virus consists essentially of heating the composition in the dry state until the composition is substantially free of said virus in the infectious form and said blood clotting enzyme in the denatured form.

49. A method for inactivating non-A, non-B hepatitis virus in a blood clotting enzyme composition suspected to contain non-A, non-B hepatitis virus, which method for inactivating non-A, non-B hepatitis virus consists essentially of heating the composition in the dry state until the composition is substantially free of said virus in the infectious form and said blood clotting enzyme in the denatured form.

50. A method for making a control or standard from blood plasma containing an infective virus, comprising removing substantially all reducing sugars from the plasma, lyophilizing the plasma and heating the lyophilized plasma until the plasma is substantially free of said virus in the infectious form and said blood clotting enzyme in the denatured form.

51. The method of claim 48 wherein reducing sugar is added to the plasma after the virus is inactivated.

52. The product produced by the method of claim 48.

53. A method for inactivating virus in a composition which contains antihemophilic factor and at least one blood clotting enzyme, and which is suspected to contain an infective virus, which method for inactivating consists essentially of heating the composition in the dry state until the composition is substantially free of said virus in the infectious form and said blood clotting enzyme in the denatured form.

54. A method for treating a dry composition containing a blood clotting enzyme purified about from 3 to 50 fold over the concentration of such enzyme in normal human plasma. and suspected to contain an infective virus, which method comprises heating the composition in the dry state until the composition is substantially free of said virus in the infectious form and said blood clotting enzyme in the denatured form.

55. The method of claim 54 wherein the virus is hepatitis A, B or non-A, non-B.

56. The method of claims 53 or 54 wherein the composition includes a stabilizing amount of a non-reducing monosaccharide, oligosaccharide, sugar alcohol or amino acid.

57. In a method wherein a therapeutically effective amount of a blood clotting enzyme is infused into a patient, the improvement comprising infusing into said patient a composition containing noninfectious virus and a therapeutically effective amount of said enzyme, which composition is substantially free of said virus in the infectious form and substantially free of said enzyme in the denatured form.

58. A method for inactivating virus in a composition comprising at least one blood clotting enzyme in a therapeutically effective amount, which method comprises heating the composition in the dry state until the composition is substantially free of said virus in the infectious form and said blood clotting enzyme in the denatured form.

59. The method of claim 54, 57 or 58 wherein the composition also contains antihemophilic factor.

60. A composition containing noninfectious virus and at least one human blood clotting enzyme, said virus having been made noninfectious by a method consisting essentially of heating the virus until the virus is inactivated, which composition is substantially free of said virus in the infectious form, is substantially free of said blood clotting enzyme in the denatured form and which contains viral residues which are partially immunologically cross-reactive with the infectious virus.

61. The composition of claim 60 wherein the virus is hepatitis A, B or non-A, non-B.

62. The composition of claim 61 wherein the enzyme is prothrombin.

63. The composition of claim 61 wherein the enzyme is factor VII.

64. The composition of claim 61 wherein the enzyme is factor IX.

65. The composition of claim 61 wherein the enzyme is factor X.

66. The composition of claim 61 wherein the enzyme is factor XI.

67. The composition of claim 61 wherein the enzyme is Hageman factor.

68. The composition of claim 61 wherein the enzyme is activated factor VII.

69. The composition of claim 61 wherein the enzyme is activated factor IX.

70. The composition of claim 61 wherein the enzyme is activated factor X.

71. The composition of claim 61 wherein the enzyme is activated factor XI.

72. The composition of claim 61 wherein the enzyme is activated Hageman factor.

73. The composition of claim 61 wherein the composition contains factor IX and is substantially free of other blood clotting enzymes.

74. The composition of claim 61 wherein the composition is substantially unactivated prothrombin complex.

75. The composition of claim 61 wherein the composition is activated prothrombin complex.

76. The composition of claim 61 which is sterile.

77. The composition of claim 61 which is in the dry state.

78. A composition containing noninfectious hepatitis A virus having been made noninfectious by a method consisting essentially of heating the virus until the virus is inactivated, which composition is substantially free of said virus in the infectious form, is substantially free of said blood clotting enzyme in the denatured form and which contains viral residues which are partially immunologically cross-reactive with hepatitis A infectious virus.

79. A composition containing noninfectious hepatitis B virus and at least one blood clotting enzyme, said virus having been made noninfectious by a method consisting essentially of heating the virus until the virus is inactivated, which composition is substantially free of said virus in the infectious form, is substantially free of said blood clotting enzyme in the denatured form and which contains viral residues which are partially immunologically cross-reactive with hepatitis B infectious virus.

80. A composition containing noninfectious non-A, non-B hepatitis virus and at least one blood clotting enzyme, said virus having been made noninfectious by a method consisting essentially of heating the virus until the virus is inactivated, which composition is substantially free of said virus in the infectious form, is substantially free of said blood clotting enzyme in the denatured form and which contains viral residues which are partially immunologically cross-reactive with non-A, non-B hepatitis virus.

81. A composition containing noninfectious virus, antihemophilic factor and at least one blood clotting enzyme, said virus having been made noninfectious by a method consisting essentially of heating the virus until the virus is inactivated, which composition is substantially free of said virus in the infectious form and said blood clotting enzyme and antihemophilic factor in the denatured form.

82. A composition containing noninfectious virus and at least one blood clotting enzyme in a purification of about from 3- to 50-fold over the concentration of such enzyme in normal human plasma, which composition is substantially free of said virus in the infectious form and said enzyme in the denatured form.

83. A composition comprising noninfectious virus and a therapeutically effective amount of at least one blood clotting enzyme, said composition being substantially free of said virus in the infectious form and substantially free of said blood clotting enzyme in the denatured form.

84. The composition of claim 60, wherein no more than about 10 mole percent of the total enzyme consists of denatured enzyme.

85. The composition of claims 60, 81, 82 or 83 containing no more than about 5 mole percent of denatured enzyme based on the total moles of denatured and active enzyme.

86. The composition of claims 60, 81, 82 or 83 containing viral residues which are partially immunologically cross-reactive with the infectious virus.

87. The composition of claims 60, 78, 80, 81, 82 or 83 which contains denatured viral epitopic sites.

* * * * *